(12) United States Patent
Chartrand et al.

(10) Patent No.: US 10,493,257 B2
(45) Date of Patent: Dec. 3, 2019

(54) PORT RESERVOIR CLEANING SYSTEM AND METHOD

(71) Applicant: AngioDynamics, Inc., Latham, NY (US)

(72) Inventors: Bradley D. Chartrand, Saratoga Springs, NY (US); Jeffrey Willis, Gansevoort, NY (US)

(73) Assignee: AngioDynamics, Inc., Latham, NY (US)

( * ) Notice: Subject to any disclaimer, the term of this patent is extended or adjusted under 35 U.S.C. 154(b) by 103 days.

(21) Appl. No.: 15/628,696

(22) Filed: Jun. 21, 2017

(65) Prior Publication Data

US 2018/0008809 A1 Jan. 11, 2018

Related U.S. Application Data

(63) Continuation of application No. 13/852,257, filed on Mar. 28, 2013, now Pat. No. 9,713,704.

(51) Int. Cl.
*A61M 39/02* (2006.01)
*A61B 17/34* (2006.01)
*A61B 90/70* (2016.01)

(52) U.S. Cl.
CPC ..... *A61M 39/0208* (2013.01); *A61B 17/3417* (2013.01); *A61B 90/70* (2016.02); *A61B 2017/3437* (2013.01); *A61B 2017/3441* (2013.01)

(58) Field of Classification Search
None
See application file for complete search history.

(56) References Cited

U.S. PATENT DOCUMENTS

| 5,312,332 A | * | 5/1994 | Bales | A61B 17/00234 |
| | | | | 604/28 |
| 5,951,512 A | * | 9/1999 | Dalton | A61M 39/0208 |
| | | | | 604/175 |

* cited by examiner

*Primary Examiner* — Eric W Golightly
(74) *Attorney, Agent, or Firm* — Peter J. Flora, Esq.

(57) ABSTRACT

Devices and methods for cleaning a port, including a port reservoir and other aspects of the port, whereby a trocar/cannula assembly is introduced to the port reservoir. The trocar is withdrawn from the port reservoir, providing access to the reservoir. A cleaning member is then advanced through the cannula, and can remove an unwanted material therefrom.

13 Claims, 7 Drawing Sheets

PORT RESERVOIR CLEANING SYSTEM AND METHOD

CROSS-REFERENCE TO RELATED APPLICATIONS

This application claims priority to U.S. non-provisional application Ser. No. 13/852,257, filed on Mar. 28, 2013, and issued as U.S. Pat. No. 9,713,704 on Jul. 25, 2017, which claims priority to U.S. provisional application No. 61/617,219 filed on Mar. 29, 2012, both of which are incorporated herein by reference in its entirety.

FIELD OF THE INVENTION

The present invention relates generally to a system and method for clearing thrombus formations from the reservoir of an implantable port.

BACKGROUND OF THE INVENTION

Medical professionals often use implantable ports for accessing the vascular system. Ports are typically implanted in the chest and connected to a catheter having a tip positioned at a particular point within the body, commonly the junction of the superior vena cava and the right atrium. Ports can have one or more reservoirs in fluid communication with one or more lumens of the catheter. A needle-penetrable and self-sealing septum covers the reservoir, and the reservoir can be accessed with a needle. The needle can be used for infusing or aspirating fluid to and from the tip of the catheter via the reservoir.

The presence of blood within the reservoir commonly leads to thrombus formation as blood platelets adhere and accumulate to the walls of the reservoir. Thrombus formations can occlude the outlet lumen and lead to increased infection rates. Occlusions can affect medical device performance, impairing the ability to infuse or aspirate fluid through the device. When port performance is compromised, medical professionals are often forced to replace the port with a new one, requiring additional surgeries, and increasing costs and risk to the patient. Further, even when the reservoir is only partially occluded, fluid dynamics within the reservoir are suboptimal. There remains a need to reduce the presence of thrombus formation within a port reservoir while minimizing costs and risks to the patient.

SUMMARY OF THE INVENTION

In one aspect, the invention provides a port reservoir cleaning system including a trocar having a proximal end and distal end, the distal end terminating in a sharp tip, a cannula having a proximal end, a distal end and a cannula lumen extending therebetween, and a cleaning member having a proximal end, a distal end, a shaft and a cleaning member lumen extending therebetween. A portion of the distal end of the shaft is flexible.

In another aspect, the invention provides a method for cleaning a port reservoir, the method including providing a port reservoir cleaning system, the system including a trocar, a cannula and a cleaning member having a shaft, where a portion of the distal end of the shaft is flexible. The trocar and cannula are advanced as an assembly through a septum fluidly sealing the port reservoir while the trocar is loaded within a lumen of the cannula. The trocar is withdrawn from the cannula lumen. The distal end of the cleaning member is advanced through the cannula lumen and into the reservoir. The cleaning member is rotated and negative pressure is supplied to a lumen of the cleaning member.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 5A shows a trocar cannula assembly advanced through a septum and into the port reservoir; FIG. 5B shows a cannula accessing the reservoir after the trocar has been withdrawn; and FIG. 5C shows the cleaning device advanced through the cannula and into the reservoir;

DETAILED DESCRIPTION OF THE INVENTION

Figure 1:
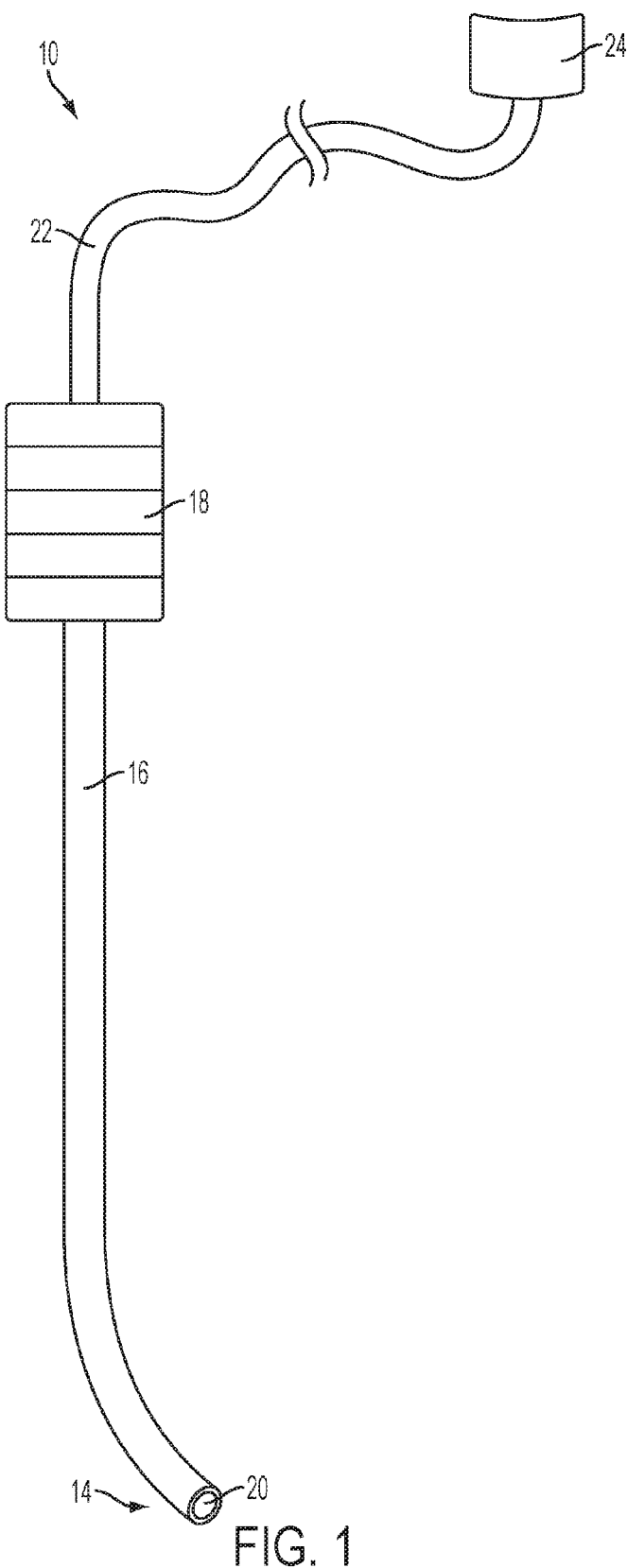
FIG. 1 is a side view of a cleaning member according to an embodiment of the invention.

The present invention can be understood more readily by reference to the following detailed description, the examples included therein, and to the Figures and their following description. The drawings, which are not necessarily to scale, depict selected preferred embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting.

Referring now in detail to the drawings, in which like reference numerals indicate like parts or elements throughout the several views, in various embodiments, presented herein is a port reservoir cleaning system and method.

As shown in FIG. 1, a cleaning member 10 according to an embodiment of the invention is formed from a polymer shaft 16 having a lumen 20 extending therethrough and terminating in an opening at the distal end 14 of the shaft 16. A hub 18 is connected to the proximal end of the shaft 16.

The lumen 20 is in fluid communication with an extension tube 22 and a connection element 24. The hub 18, extension tube 22 and connection element 24 can be made of medical grade plastics and polymers, and manufactured using extrusion and injection molding techniques known in the art.

Figure 2:
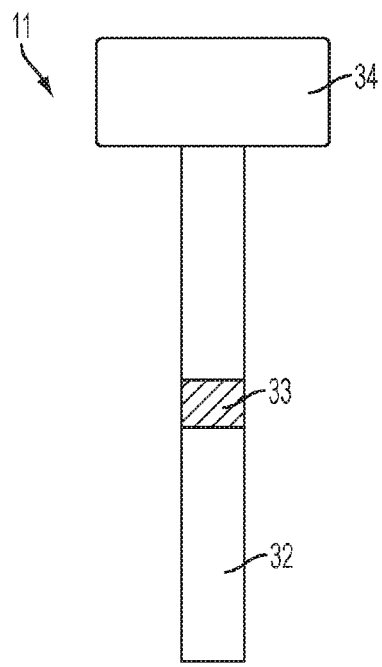
FIG. 2 is a side view of a cannula according to an embodiment of the invention.
Figure 3:
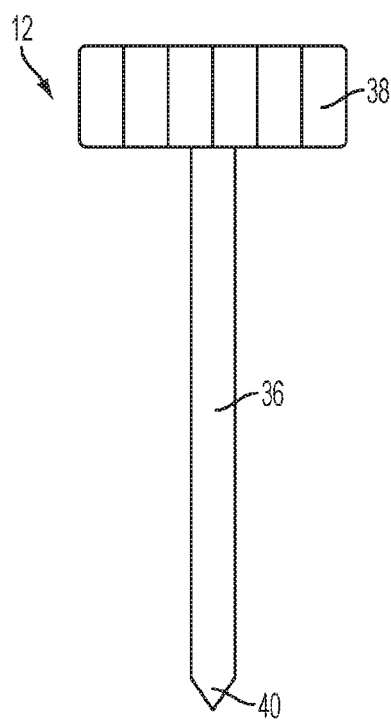
FIG. 3 is a side view of a trocar according to an embodiment of the invention.
Figure 4:
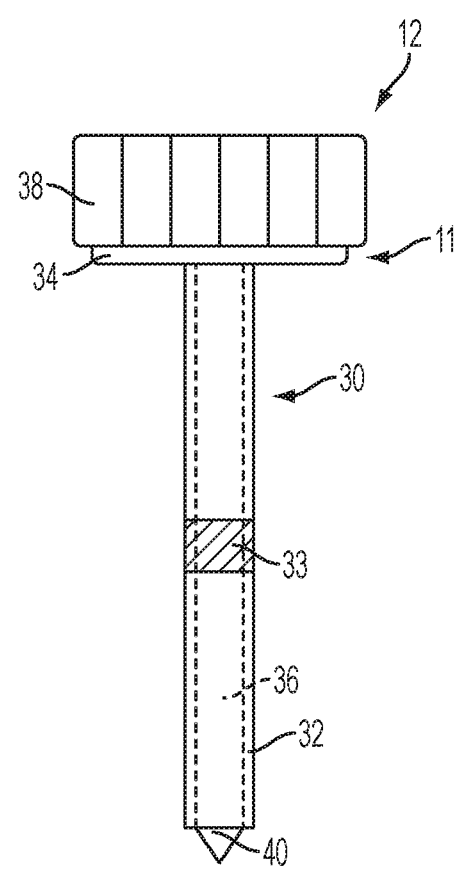
FIG. 4 is a side view of a trocar cannula assembly according to the embodiments of the invention shown in FIGS. 2 and 3.

Cleaning member 10 accesses the port reservoir via a cannula 11 and a trocar 12 as shown in FIGS. 2 and 3. The cannula 11 includes a tube 32 having a valve 33 extending across its lumen. The valve 33 is a self-sealing valve, and can be for example a slit valve or a reed valve. The cannula 11 also includes a hub 34. The trocar 12 has a shaft 36 terminating in a point 40 at its distal end, and a hub 38. The trocar and cannula can be mated as a trocar cannula assembly 30, as shown in FIG. 4. The trocar shaft 36 extends through the cannula 11 lumen such that the tip 40 of the trocar 12 extends just beyond the distal cannula opening. The outside of the hub 34 for the cannula 11 can have engaging member (such as threads) compatible with engaging members on an inside wall of the hub 38 for the trocar 12, so that they can be fixed to one another when formed as an assembly 30. The cannula and trocar shafts can be made of more rigid materials such as plastics or metals, so that they are capable of advancing though the compressed elastomeric septum without kinking or collapsing.

Figure 5A:
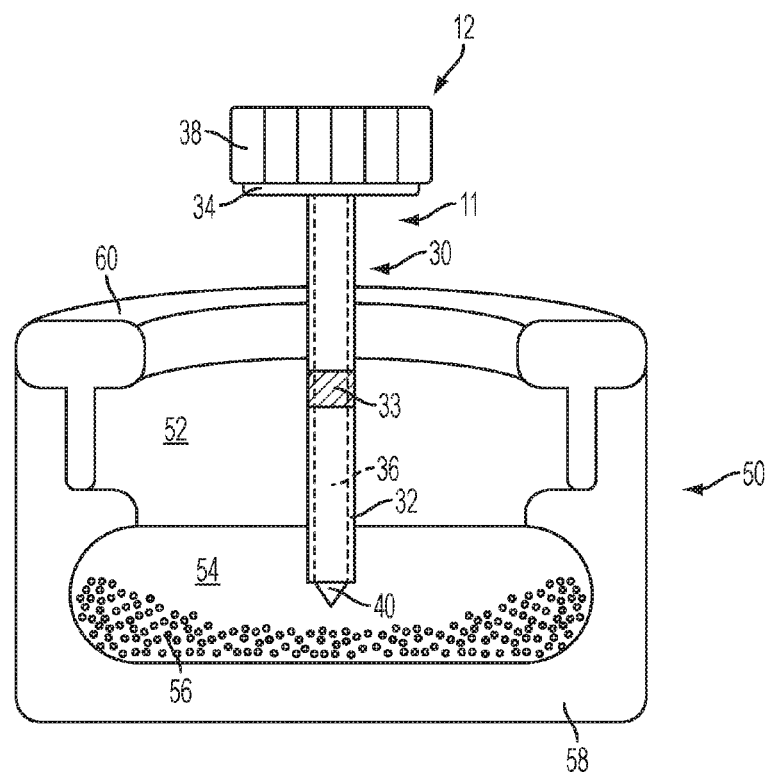
FIGS. 5A-5C show cross-sectional views of a port reservoir accessed by a system according to the embodiments of the invention shown in FIGS. 1-3.
Figure 5B:
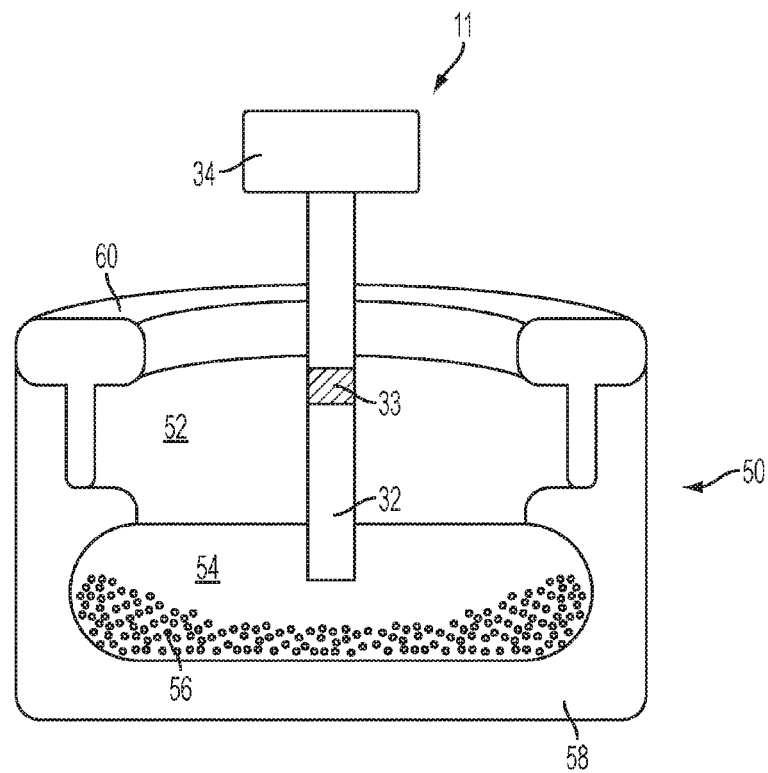
Figure 5C:
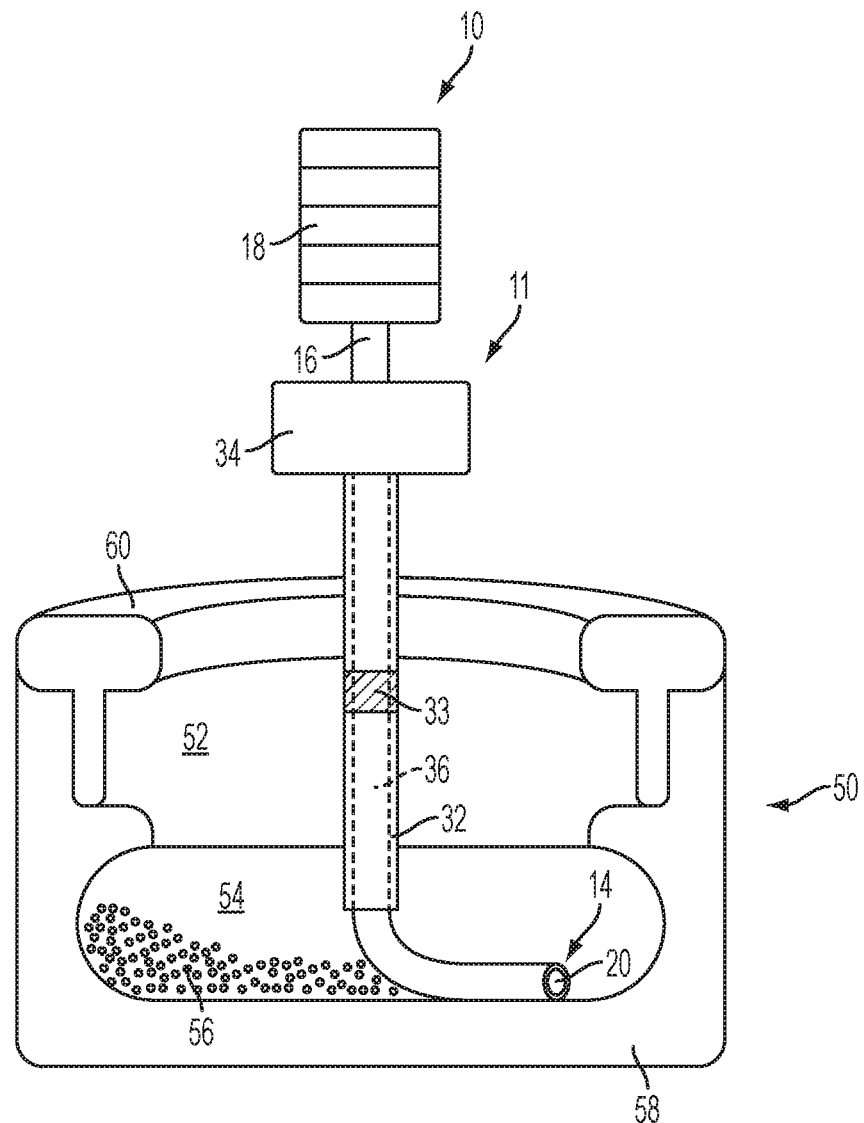

FIGS. 5A-5C illustrate how the system of the cleaning member 10, cannula 11 and trocar 12 can be used to access and clean thrombus formations from the port reservoir. As shown in FIG. 5A, a typical port 50 has a port body 58 defining one or more walls of a reservoir 54. The reservoir 54 is fluidly sealed by an elastomeric septum 52, and the septum 52 is held to the port body 58 by a retaining ring 60. To provide for the cleaning device 10 to the reservoir 54, the trocar cannula assembly 30 is advanced through the port septum 52 so that the distal ends of the assembly enter the reservoir. The trocar 12 is subsequently withdrawn from the lumen of the cannula 11, and the cannula 11 remains, providing access to the reservoir 54, as shown in FIG. 5B. Fluid access to the reservoir is sealed by the valve 33 which automatically seals upon withdrawal of the trocar 12. The cleaning member 10 is then advanced through the lumen of the cannula 11, and the distal end 14 of the cleaning device 10 can be advanced towards the side walls of the reservoir 54, as shown in FIG. 5C.

With the distal end 14 of the cleaning device 10 in fluid communication with the reservoir 54, infusion and aspiration be performed for cleaning surfaces of the reservoir 54 walls. For instance, an anti-coagulant solution such as heparinized saline can be infused into the port to chemically breakup and loosen thrombus formations. The tip of the distal end 14 of the cleaning member 10 can be used to mechanically scrape or abrade the thrombus formations 56, while a negative pressure is simultaneously applied to the cleaning device lumen 20 to aspirate loose pieces of thrombus. The scraping action can be performed by moving the cleaning device 10 in an up and down motion through the cannula 11, while rotating the device 10 to reach all surfaces. The hub 18 can include gripping features to make manipulating the device easier. Suction within the lumen 20 can be also be helpful in preventing chunks of thrombus from passing through the port catheter and into the blood stream, minimizing the risk of an embolism.

Figure 6:
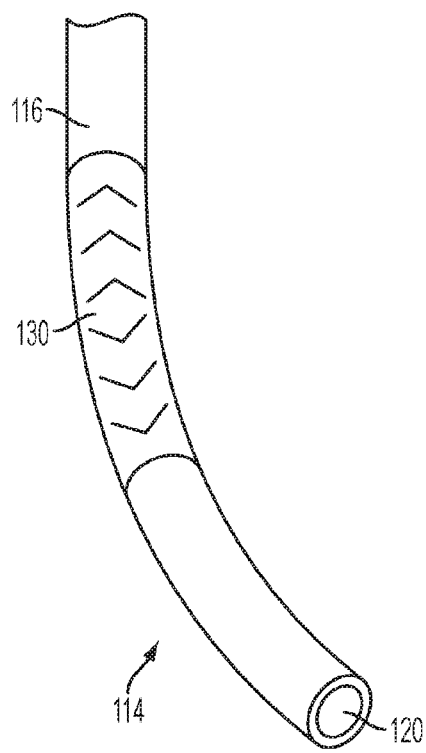
FIG. 6 shows the distal end of a cleaning device having more than one flexural modulus according to an embodiment of the invention.

The cleaning device 10 has a flexible distal end 14 which allows the device to extend outward to edges of the reservoir 54, as shown in FIG. 5C. To aid the mechanical breakup of thrombus 56, aspiration of material, and to reinforce the cannula where it flexes, a portion of the device shaft can be manufactured to have a higher flexural modulus relative to other portions of the shaft, according to an embodiment of the invention as shown in FIG. 6. If the shaft 116 is reinforced with a high flexural modulus around the flex point 130, the distal end 114 of the cleaning device will be biased towards and remain pressed up against reservoir walls. Proximity of the lumen 120 opening to the reservoir wall surfaces facilitates improved aspiration and mechanical breakup of thrombus adhered to reservoir walls. Further, kinking of the shaft 36 at the flex point can be minimized, which will facilitate better aspiration through the lumen 120. The shaft 116 can include a reinforcing technique known in the art, such as thicker shaft side wall, overmolding or co-extrusion of a reinforcing member, a transition to a higher durometer polymer, or other reinforcing techniques known in the art for providing for a higher flexural modulus. To aid insertion of a cleaning member in general, especially in embodiments having a higher flexural modulus at the flex point, the tip of the distal end 114 can taper so that as it is advanced into the reservoir and presses against the bottom surface, it tilts and falls to one side, promoting lateral movement towards a side wall.

Figure 7:
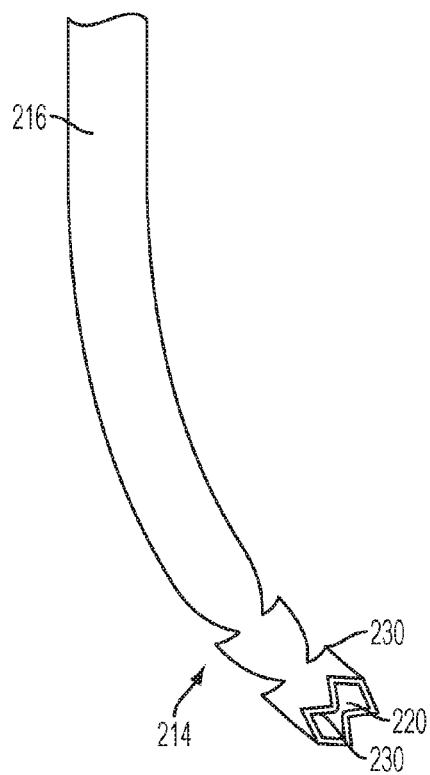
FIG. 7 shows the distal end of a cleaning device having scraping members according to an embodiment of the invention.

The distal end of the cleaning device can also incorporate scraping edges for the mechanical breakup of thrombus buildup according to an embodiment of the invention, as shown in FIG. 7. The shaft 216 can include skived elements 230 cut from the shaft walls and tip of the distal end 214. Scraping edges 230 formed around the distal tip of the lumen 220 can be especially helpful for cleaning the reservoir according to the method of mechanical breakup of thrombus with simultaneously thrombus fragments. The shaft 216 can be coextruded with a high durometer outer layer, so that skived scraping elements have rigid outer edges. Alternatively, scraping elements made of hard materials such as metals can be overmolded or affixed to the distal end 214 of the cleaning device using techniques known in the art. Side holes can be incorporated in the shaft 216 wall for fluid access to the lumen 220, or skived elements can be cut so that openings are cut into shaft 216 side walls as skives are formed. Openings can be located adjacent to scraping members 230 for advantageously aspirating thrombus as it is fragmented by scraping members 230. Hole arrays can also be arranged to uniformly distribute anti-coagulant fluid during infusion functions on inner walls of the reservoir.

Figure 8:
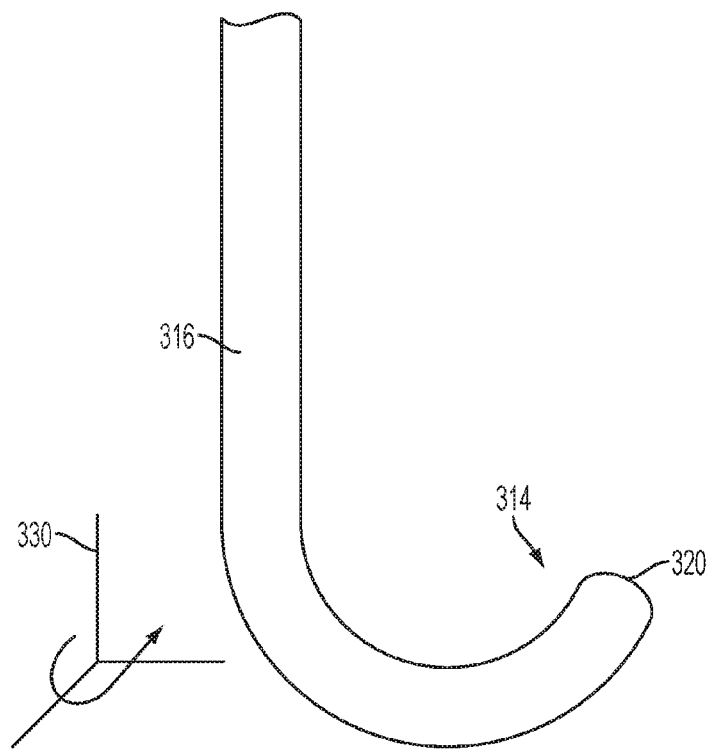
FIG. 8 shows the distal end of a cleaning device having a pre-curved end according to an embodiment of the invention.

Mechanical breakup of thrombus formations can be further facilitated by manufacturing the distal end of the cleaning member shaft in a pre-curved configuration according to an embodiment of the invention, as shown in FIG. 8. The curve can wrap around the longitudinal axis of proximal portions of the shaft 316, as illustrated in the diagram accompanying FIG. 8. With this configuration, the user can twist the device and the tip 320 of the device acts as a leading edge for following along the wall of a contoured reservoir. According to this embodiment, the mechanical breakup of thrombus on surfaces can be improved, especially along outer edges of the reservoir. This configuration, like any configuration, can be combined with others to promote contact with the reservoir wall and mechanical breakup of thrombus formations.

Figure 9:
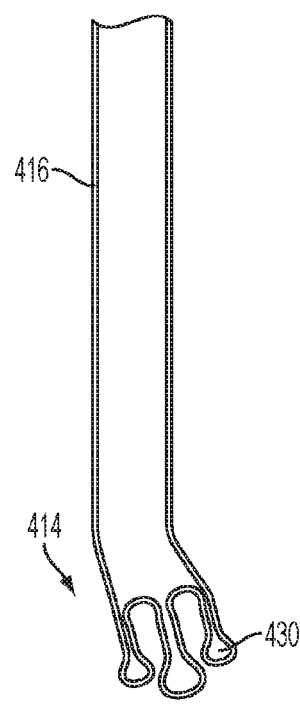
FIG. 9 shows the distal end of a wire element for use with the cleaning member according to an embodiment of the invention.

As shown in FIG. 9, a wire member 416 can be advanced through a system lumen for effectively breaking up or dislodging thrombus. The wire member 416 can have loops 430 or other types of openings at its distal end 414 which can scrape against the reservoir wall and masticate thrombus formations into smaller pieces for aspiration. This wire embodiment can also be fixed to the distal end of the cleaning member. The wire can be a medical grade metal having a shape memory such an nitinol so that the distal end 414 expands after exiting a lumen and being exposed within the reservoir. Alternatively, the wire element can be another hardened or metal element having edges capable of effectively dislodging and/or fragmenting thrombus formations within the reservoir.

The invention claimed is:

1. A method of cleaning at least one port reservoir, the method comprising:
    inserting an assembly into the at least one port reservoir by piercing a septum of the at least one port reservoir, the assembly comprising:
        a trocar comprising a trocar proximal end and a trocar distal end, the trocar distal end terminating in a sharp tip; and
        a cannula comprising a cannula proximal end, a cannula distal end and a cannula lumen extending therebetween;
    removing the trocar from the cannula; and
    inserting a cleaning member through the cannula lumen and into the at least one port reservoir, the cleaning member comprising a cleaning member proximal end, a cleaning member distal end, a cleaning member shaft and a cleaning member lumen extending between the cleaning member proximal end and the cleaning member distal end, wherein a portion of the cleaning member distal end of the cleaning member shaft is flexible.

2. The method of claim 1, wherein the cannula further comprises a valve element disposed across the cannula lumen.

3. The method of claim 1, wherein a first portion of the cleaning member shaft and a second portion of the cleaning member shaft have a different flexural modulus.

4. The method of claim 3, wherein the first portion of the cleaning member shaft and the second portion of the cleaning member shaft comprise polymers of different durometers.

5. The method of claim 4, wherein the first portion of the cleaning member shaft comprises a reinforcing member.

6. The method of claim 1, wherein the cleaning member distal end comprises a plurality of scraping members.

7. The method of claim 1, wherein the cleaning member distal end is pre-curved.

8. The method of claim 1, further comprising the step of:
    inserting a wire element through the cannula lumen beyond a cannula lumen distal opening for a selected distance.

9. The method of claim 8, wherein the wire element comprises a shape memory metal.

10. A method of cleaning at least one port reservoir, the method comprising:
    inserting an assembly into an at least one port reservoir, the assembly comprising:
        a trocar; and
        a cannula comprising a cannula lumen;
    removing the trocar from the cannula; and
    inserting a cleaning member through the cannula lumen and into the at least one port reservoir, the cleaning member comprising a cleaning member proximal end, a cleaning member distal end, a cleaning member shaft extending between the cleaning member proximal end and the cleaning member distal end, wherein a portion of the cleaning member distal end of the cleaning member shaft is flexible.

11. The method of claim 10, wherein the assembly is inserted into the at least one port reservoir by piercing a septum of the at least one port reservoir.

12. The method of claim 10, wherein a trocar distal end terminates in a sharp tip.

13. A method of cleaning at least one port reservoir, the method comprising:
    inserting an assembly into the at least one port reservoir, the assembly comprising a cannula comprising a cannula lumen; and
    inserting a cleaning member through the cannula lumen and into the at least one port reservoir, the cleaning member comprising a cleaning member proximal end, a cleaning member distal end, and a cleaning member shaft extending between the cleaning member proximal end and the cleaning member distal end, wherein a portion of the cleaning member distal end of the cleaning member shaft is flexible.

* * * * *